United States Patent
Honorat et al.

(10) Patent No.: US 11,493,513 B2
(45) Date of Patent: Nov. 8, 2022

(54) ASSESSING AND TREATING AUTOIMMUNE ATAXIA

(71) Applicant: Mayo Foundation for Medical Education and Research, Rochester, MN (US)

(72) Inventors: Josephe A. Honorat, Rochester, MN (US); Andrew McKeon, Rochester, MN (US); Sean J. Pittock, Rochester, MN (US); Vanda A. Lennon, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 52 days.

(21) Appl. No.: 15/733,710

(22) PCT Filed: May 21, 2019

(86) PCT No.: PCT/US2019/033254
§ 371 (c)(1),
(2) Date: Oct. 1, 2020

(87) PCT Pub. No.: WO2019/226616
PCT Pub. Date: Nov. 28, 2019

(65) Prior Publication Data
US 2021/0311047 A1    Oct. 7, 2021

Related U.S. Application Data

(60) Provisional application No. 62/674,347, filed on May 21, 2018.

(51) Int. Cl.
*G01N 33/564* (2006.01)
*A61K 39/00* (2006.01)

(52) U.S. Cl.
CPC ....... *G01N 33/564* (2013.01); *A61K 39/0008* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 2014/0141449 A1 | 5/2014 | Sarwal et al. | |
| 2018/0110912 A1 | 4/2018 | Henley | |

FOREIGN PATENT DOCUMENTS

| | | |
|---|---|---|
| EP | 3086120 | 10/2016 |
| WO | 2012139051 | 10/2012 |
| WO | 2016/189163 | 12/2016 |
| WO | 2016/205681 | 12/2016 |
| WO | 2018/048884 | 3/2018 |
| WO | 2018/063792 | 4/2018 |

OTHER PUBLICATIONS

Bahtz et al., "Identification of septin complex as an autoantibody target in paraneoplastic cerebellar ataxia," Journal of Neuroimmunology; Oct. 15, 2014, vol. 275, Issue 1-2, p. 37.
Honorat et al., "Autoimmune Septin-5 Cerebellar Ataxia," Neurol Neuroimmunology & Neuroinflammation, Sep. 2018, vol. 5, No. 5, pp. 1-6.
Ariño et al., "Cerebellar Ataxia and Glutamic Acid Decarboxylase Antibodies", JAMA Neurology, vol. 71, No. 8, Aug. 2014, pp. 1009-1016.
Jarious et al., "'Medusa head ataxia': the expanding spectrum of Purkinje cell antibodies in autoimmune cerebellar ataxia. Part 3: Anti-Yo/CDRZ, anti-Nb/AP3B2, PCA-2, anti-Tr/DNER, other antibodies, diagnostic pitfalls, summary and outlook", Journal of Neuroinflammation, vol. 12, No.168, 2015, pp. 1-22.

*Primary Examiner* — G. R. Ewoldt
(74) *Attorney, Agent, or Firm* — Grüneberg and Myers PLLC

(57) ABSTRACT

Methods and materials herein are useful for assessing and/or treating autoimmune ataxias associated with septin-specific autoantibodies (e.g., septin-5-specific autoantibodies). For example, septin-5 polypeptides are provided as well as methods for using septin-5 polypeptides to detect septin-5-specific autoantibodies and/or to treat a mammal having an autoimmune ataxia.

3 Claims, 6 Drawing Sheets

Specification includes a Sequence Listing.

SEQ ID NO:1

MSTGLRYKSKLATPEDKQDIDKQYVGFATLPNQVHRK
SVKKGFDFTLMVAGESGLGKSTLVHSLFLTDLYKDRK
LLSAEERISQTVEILKHTVDIEEKGVKLKLTIVDTPG
FGDAVNNTECWKPITDYVDQQFEQYFRDESGLNRKNI
QDNRVHCCLYFISPFGHGLRPVDVGFMKALHEKVNIV
PLIAKADCLVPSEIRKLKERIREEIDKFGIHVYQFPE
CDSDEDEDFKQQDRELKESAPFAVIGSNTVVEAKGQR
VRGRLYPWGIVEVENQAHCDFVKLRNMLIRTHMHDLK
DVTCDVHYENYRAHCIQQMTSKLTQDSRMESPIPILP
LPTPDAETEKLIRMKDEELRRMQEMLQRMKQQMQDQ

FIG. 4

```
SEQ ID NO:2

MDRSLGWQGNSVPEDRTEAGIKRFLEDTTDDGELSKF
VKDFSGNASCHPPEAKTWASRPQVPEPRPQAPDLYDD
DLEFRPPSRPQSSDNQQYFCAPAPLSPSARPRSPWGK
LDPYDSSEDDKEYVGFATLPNQVHRKSVKKGFDFTLM
VAGESGLGKSTLVNSLFLTDLYRDRKLLGAEERIMQT
VEITKHAVDIEEKGVRLRLTIVDTPGFGDAVNNTECW
KPVAEYIDQQFEQYFRDESGLNRKNIQDNRVHCCLYF
ISPFGHGLRPLDVEFMKALHQRVNIVPILAKADTLTP
PEVDHKKRKIREEIEHFGIKIYQFPDCDSDEDEDFKL
QDQALKESIPFAVIGSNTVVEARGRRVRGRLYPWGIV
EVENPGHCDFVKLRTMLVRTHMQDLKDVTRETHYENY
RAQCIQSMTRLVVKERNRNKLTRESGTDFPIPAVPPG
TDPETEKLIREKDEELRRMQEMLHKIQKQMKENY
```

FIG. 5

ASSESSING AND TREATING AUTOIMMUNE ATAXIA

CROSS-REFERENCE TO RELATED APPLICATIONS

This application is a National Stage entry under § 371 of International Application No. PCT/US2019/033254 filed on May 21, 2019, and claims the benefit of U.S. Provisional Patent Application Ser. No. 62/674,347, filed on May 21, 2018. The content of each of these applications is hereby incorporated by reference in its entirety.

REFERENCE TO A SEQUENCE LISTING

The present application is accompanied by an ASCII text file as a computer readable form containing the sequence listing, titled "2020-08-27-Sequence Listing_ST25.txt" created on Aug. 27, 2020 with the file size of 7,664 bytes, which is incorporated by reference in its entirety.

BACKGROUND

1. Technical Field

This document relates to methods and materials for assessing and treating autoimmune ataxias associated with septin-specific autoantibodies (e.g., septin-5-specific autoantibodies). For example, this document relates to methods and materials for using septin-5 polypeptides (or fragments thereof) to detect the presence or absence of septin-5-specific autoantibodies.

2. Background Information

Cerebellar degeneration leads to disability from loss of balance, incoordination and speech impairment, and also can affect cognitive function (Hoche et al., 2017 *Brain* 88 (16 Supplement):206). Testing for an autoimmune cause is an important diagnostic endeavor in affected patients, particularly those with a subacute onset and rapidly progressive course (Jones et al., 2015 *JAMA Neurol.* 72:1304-1312).

SUMMARY

This document provides methods and materials for detecting autoimmune ataxias (e.g., autoimmune cerebellar ataxias) associated with septin-specific autoantibodies (e.g., septin-5-specific autoantibodies) as well as methods and materials for treating autoimmune ataxias associated with septin-specific autoantibodies (e.g., septin-5-specific autoantibodies).

As demonstrated herein, patients with immunotherapy-responsive autoimmune cerebellar ataxia exhibited a presence of septin-5-specific autoantibodies (e.g., septin-5-IgG) in serum and cerebrospinal fluid (CSF) samples. Also as demonstrated herein, a recombinant form of septin-5 polypeptide was able to detect the presence of septin-5-IgG in both serum and tissue.

The detection of septin-5-specific autoantibodies can be used to support a diagnosis of autoimmune ataxia associated with septin-5-specific autoantibodies, such as autoimmune cerebellar ataxias. In some cases, a septin-5 polypeptide can be used to treat autoimmune ataxia associated with septin-5-specific autoantibodies, such as autoimmune cerebellar ataxias.

In general, one aspect of this document features methods for detecting the presence or absence of a septin-5-specific autoantibody in a biological sample from a mammal. The methods can include, or consist essentially of contacting a biological sample from a mammal with a septin-5 polypeptide to form a septin-5/septin-5-specific autoantibody complex if the biological sample contains septin-5-specific autoantibodies, and detecting the presence or absence of the septin-5/septin-5-specific autoantibody complex. The method can include detecting the presence of the complex. The presence of the septin-5-specific autoantibody in the biological sample can be associated with autoimmune ataxia associated with septin-5-specific autoantibodies in the mammal. The autoimmune ataxia can be an autoimmune cerebellar ataxia. The method can include performing a western blot to detect the complex. The biological sample can be whole blood, serum, plasma, or cerebrospinal fluid.

In another aspect, this document features a kit include a septin-5 polypeptide and an anti-IgG antibody. The anti-IgG antibody can be an anti-human IgG antibody. The kit anti-human IgG antibody can include a covalently attached label. The kit can include an anti-septin-5 antibody. The septin-5 antibody can be an anti-human septin-5 antibody.

In another aspect, this document features methods for treating a mammal having an autoimmune ataxia associated with septin-5-specific autoantibodies. The methods can include, or consist essentially of, withdrawing a biological fluid from the mammal, where the biological fluid contains septin-5-specific autoantibodies, contacting the biological fluid with a septin-5 polypeptide to remove a substantial portion of said septin-5-specific autoantibodies from the biological fluid, and returning the biological fluid to the mammal. The mammal can be a human. The biological fluid can include blood. The autoimmune ataxia can be an autoimmune cerebellar ataxia.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

A specific IgG autoantibody is found in serum of patients presenting with immunotherapy-responsive autoimmune ataxias. The target of this IgG autoantibody was identified as a septin (e.g., septin-5), a synaptic protein that functions in, for example, cytokinesis, diffusion barrier formation, release of neurotransmitters, microtubule dynamics, and host-bacterium interactions, and is found throughout the mammalian central nervous system (e.g., in the hippocampus, thalamus, and cerebellum) and the peripheral nervous system (e.g., in enteric neurons and renal glomeruli), as well as in platelets.

This document provides methods and materials for assessing and/or treating a mammal having, or suspected of having, an autoimmune ataxia. A mammal having an autoimmune ataxia associated with septin-specific autoantibodies can have an immune system that is producing septin-specific autoantibodies. For example, a mammal (e.g., a human) having an autoimmune ataxia associated with septin-5-specific autoantibodies can have an immune system that is producing septin-5-specific autoantibodies. In some cases, this document provides septin polypeptides (e.g., septin-5 polypeptides) having at least one antigenic site recognized by a septin-specific autoantibody (e.g., a septin-specific autoantibody produced by the immune system of a mammal having an autoimmune ataxia). In some cases, one or more septin polypeptides (e.g., one or more septin-5 polypeptides) provided herein can be used to detect the presence or absence septin-specific autoantibodies (e.g., septin-5-specific autoantibodies) in a sample (e.g., a blood sample obtained from a human). For example, one or more septin polypeptides (e.g., one or more septin-5 polypeptides) can be used to assess a sample obtained from a mammal having, or suspected of having, an autoimmune ataxia for the presence or absence of septin-specific autoantibodies (e.g., septin-5-specific autoantibodies). The presence of septin-specific autoantibodies can be used to identify (e.g., diagnose) a mammal as having an autoimmune ataxia (e.g., an autoimmune cerebellar ataxia) associated with septin-specific autoantibodies.

In some cases, one or more septin polypeptides (e.g., one or more septin-5 polypeptides) provided herein can be used to treat a mammal having, or suspected of having, an autoimmune ataxia. For example, one or more septin polypeptides (e.g., one or more septin-5 polypeptides) can be administered to a mammal having, or suspected of having, an autoimmune ataxia to treat the mammal.

Any appropriate mammal can be assessed as described herein (e.g., assessed for the presence or absence of septin-specific autoantibodies) and/or treated as described herein (e.g., treated with one or more septin polypeptides such as septin-5 polypeptides). Examples of mammals that can be assessed as described herein and/or treated as described herein include, without limitation, humans, non-human primates, monkeys, bovine species, pigs, horses, dogs, cats, rats, and mice. For example, a human can be assessed for the presence or absence of septin-specific autoantibodies (e.g., septin-5-specific autoantibodies) as described herein. In some cases, a human identified as having an autoimmune ataxia and as having septin-specific autoantibodies can be treated with one or more septin polypeptides (e.g., septin-5 polypeptides) as described herein.

Any appropriate sample from a mammal (e.g., a human) can be assessed as described herein (e.g., assessed for the presence or absence of septin-specific autoantibodies). Examples of samples (e.g., biological samples) that can be assessed as described herein include, without limitation, biological fluids (e.g., blood such as whole blood, serum, or plasma, urine, cerebrospinal fluid, synovial fluid, or saliva) and biological tissues (e.g., brain tissue such as tissue obtained from a brain biopsy). For example, serum can be obtained from a mammal and assessed for the presence or absence of septin-specific autoantibodies (e.g., septin-5-specific autoantibodies).

A mammal having any appropriate type of autoimmune ataxia can be assessed (e.g., for the presence or absence of septin-specific autoantibodies such as septin-5-specific autoantibodies) and/or treated (e.g., by administering a septin polypeptide to the mammal) using the methods and materials described herein. In some cases, an autoimmune ataxia can be a severe ataxia. In some cases, an autoimmune ataxia can be a rapidly progressive ataxia. In some cases, an autoimmune ataxia can be a paraneoplastic ataxia (e.g., can be associated with, can be a symptom of, or can be a complication of a cancer). For example, an autoimmune ataxia can be associated with a neuroendocrine tumor (e.g., neuroendocrine pancreatic tumor). An autoimmune ataxia can affect any appropriate part of a mammal's nervous system (e.g., a part of the nervous system that coordinates movement) such as the cerebellum (e.g., cerebellar ataxia), dorsal columns (e.g., sensory ataxia), or vestibular system (e.g., vestibular ataxia). In some cases, an autoimmune ataxia can be an autoimmune cerebellar ataxia. For example, a mammal having an autoimmune cerebellar ataxia can be assessed and/or treated using the methods and materials described herein.

Any appropriate septin polypeptide can be used as described herein (e.g., to detect the presence or absence septin-specific autoantibodies and/or to treat a mammal having, or suspected of having, an autoimmune ataxia). For example, in humans, a septin polypeptide can be a septin-1 polypeptide, a septin-2 polypeptide, a septin-3 polypeptide, a septin-4 polypeptide, a septin-5 polypeptide, a septin-6 polypeptide, a septin-7 polypeptide, a septin-8 polypeptide, a septin-9 polypeptide, a septin-10 polypeptide, a septin-11 polypeptide, a or septin-12 polypeptide. In some cases, a septin polypeptide can be a septin-5 polypeptide. In some cases, a septin polypeptide can be a septin-4 polypeptide. In some cases, a full length septin polypeptide (e.g., a full length septin-5 polypeptide) can be used to assess a sample for the presence or absence of septin-specific autoantibodies such as septin-5-specific autoantibodies. In some cases, a fragment of a septin polypeptide (e.g., a fragment of a septin-5 polypeptide) can be used to assess a sample for the presence or absence of septin-specific autoantibodies such as septin-5-specific autoantibodies. For example, a fragment of a septin polypeptide containing one or more epitopic sites (e.g., B cell epitopes) can be used to assess a sample for the presence or absence of septin-specific autoantibodies such as septin-5-specific autoantibodies. Examples of fragments of a septin polypeptide that can be used to assess a sample for the presence or absence of septin-specific autoantibodies include, without limitation, those fragments set for this Table 1.

TABLE 1

Human septin polypeptide fragments.

| Name of septin-4 fragment | First amino acid residue[#] | Last amino acid residue[#] |
| --- | --- | --- |
| J3QRS4_Human | 21 | 72 |

| Name of septin-5 fragment | First amino acid residue[##] | Last amino acid residue[##] |
| --- | --- | --- |
| F8W9E5_Human | 48 | 227 |
| C9JM82_Human | 48 | 301 |
| E7QM7_Human | 1 | 248 |

[#]numbering is based on amino acid sequence of Genbank Accession Number NP_004565.1.
[##]numbering is based on amino acid sequence of Genbank Accession Number NP_002679.2.

Figure 5:
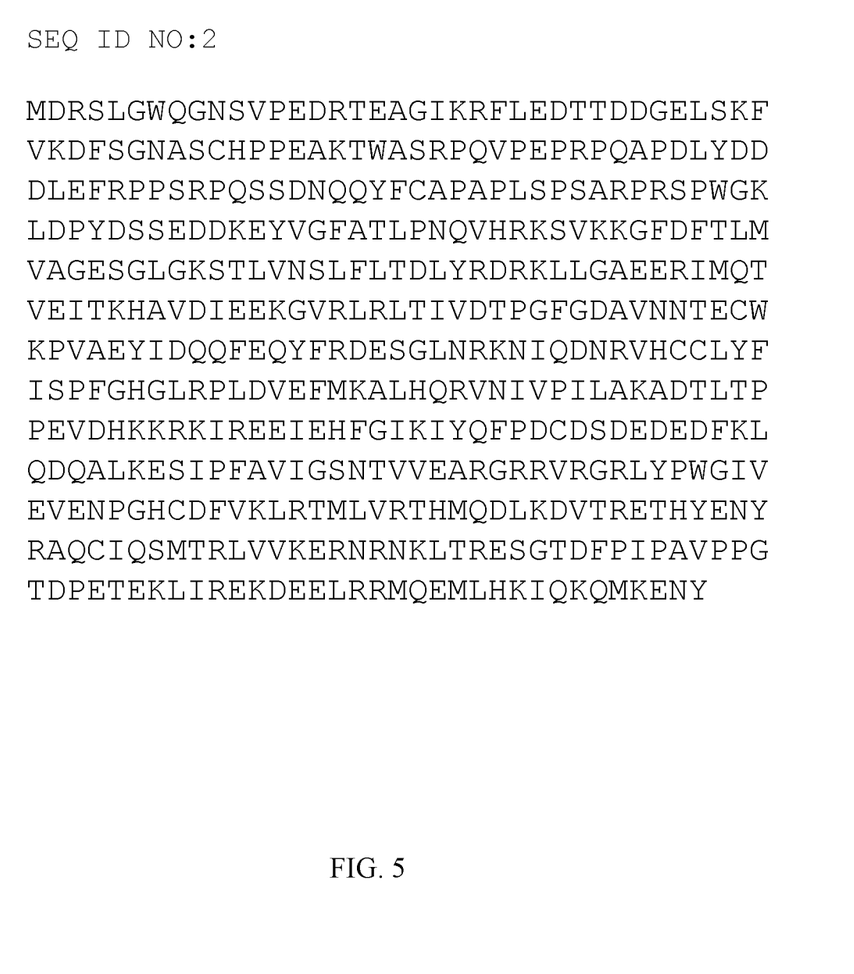
FIG. 5 shows an exemplary septin-4 polypeptide sequence (SEQ ID NO:2).

In some cases, a septin-4 polypeptide can be used as described herein (e.g., to detect the presence or absence septin-specific autoantibodies and/or to treat a mammal having, or suspected of having, an autoimmune ataxia). Examples of septin-4 polypeptide sequences (and the nucleic acids encoding such polypeptides) can be found in the National Center for Biotechnology Information (NCBI) databases (e.g., Gen Pept and GenBank). Examples of human septin-4 polypeptide sequences include, without limitation, NCBI Accession Nos. NP_536341 (Version No. NP_536341.1), NP_004565 (Version No. NP_004565.1), NP_536340 (Version No. NP_536340.1), and NP_001185642 (Version No. NP_001185642.1). Additional septin-4 sequences can be found, for example, in public databases. A representative human septin-4 sequence is as shown in FIG. 5 (SEQ ID NO:2). In some cases, a fragment of a septin-4 polypeptide can be used as described herein. Examples of fragments of septin-4 fragments that can be used to detect a septin-4-specific autoantibody can include, without limitation, those fragments set forth in Table 1.

Figure 4:
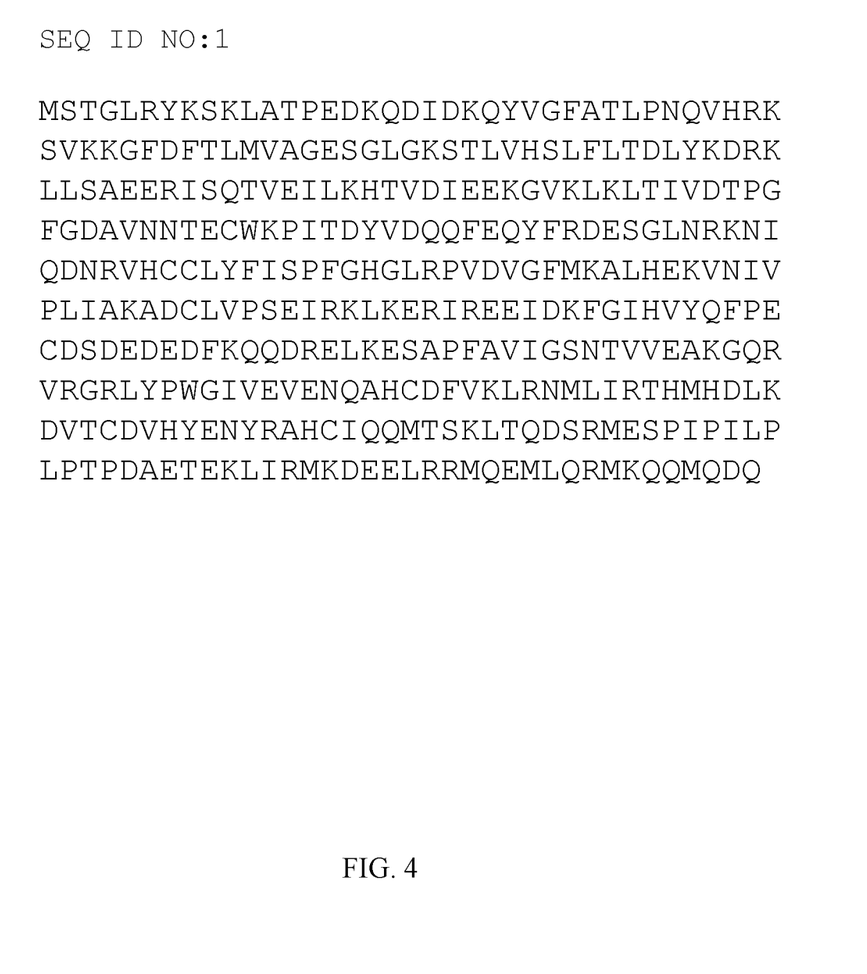
FIG. 4 shows an exemplary septin-5 polypeptide sequence (SEQ ID NO:1).

In some cases, a septin-5 polypeptide can be used as described herein (e.g., to detect the presence or absence septin-specific autoantibodies and/or to treat a mammal having, or suspected of having, an autoimmune ataxia). A septin-5 polypeptide can be any appropriate isoform of septin-5. In some cases, a septin-5 can be a septin-5-variant 1 (v1) (e.g., a full-length septin-5 polypeptide). In some cases, a septin-5 can be a septin-5 v2 (e.g., a septin-5 polypeptide having a truncated N-terminus). Examples of septin-5 polypeptide sequences (and the nucleic acids encoding such polypeptides) can be found in the NCBI databases (e.g., Gen Pept and GenBank). Examples of human septin-5 polypeptide sequences include, without limitation, NCBI Accession Nos. NP_002679 (Version No. NP_002679.2; SEQ ID NO:1), NP_001009939 (Version No. NP_001009939.1), and AHW56397 (Version No. AHW56397.1). Additional septin-5 sequences can be found, for example, in public databases. A representative human septin-5 sequence is as shown in FIG. 4 (SEQ ID NO:1). In some cases, a fragment of a septin-5 polypeptide can be used as described herein. Examples of fragments of septin-5 polypeptides that can be used to detect a septin-5-specific autoantibody can include, without limitation, those set forth in Table 1.

This document also provides nucleic acids and constructs encoding septin polypeptides described herein (e.g., septin-5 polypeptides) or fragments of septin polypeptide described herein. As used herein, nucleic acid can refer to RNA, DNA, or a combination thereof. In some cases, a nucleic acid encoding a septin polypeptide or fragment of a septin polypeptide described herein can be an isolated nucleic acid. As used herein with respect to nucleic acids, "isolated" refers to (i) a nucleic acid sequence encoding all or part of a septin polypeptide, but free of coding sequences that normally flank one or both sides of the nucleic acid sequences encoding the septin in the genome; or (ii) a nucleic acid incorporated into a vector or into the genomic DNA of an organism such that the resulting molecule is not identical to any naturally-occurring vector or genomic DNA. In some cases, a nucleic acid provided herein can encode a fragment of a septin polypeptide where the fragment is a fragment set forth in Table 1.

In some cases, a septin polypeptide that can be used as described herein (e.g., to detect the presence or absence septin-specific autoantibodies and/or to treat a mammal having, or suspected of having, an autoimmune ataxia) can have a sequence that deviates from a wild type septin polypeptide sequence, sometimes referred to as a variant sequence. For example, a septin polypeptide sequence can have at least 80% sequence identity to SEQ ID NO:1 provided that it includes one or more amino acid additions, subtractions, or substitutions compared to SEQ ID NO:1. In some embodiments, a septin polypeptide sequence can have at least 85% sequence identity, 90% sequence identity, 95% sequence identity, or at least 99% sequence identity to SEQ ID NO:1 provided that it includes one or more amino acid additions, subtractions, or substitutions compared to SEQ ID NO:1. Percent sequence identity is calculated by determining the number of matched positions in aligned nucleic acid or polypeptide sequences, dividing the number of matched positions by the total number of aligned nucleotides or amino acids, respectively, and multiplying by 100. A matched position refers to a position in which identical nucleotides or amino acids occur at the same position in aligned sequences. The total number of aligned nucleotides or amino acids refers to the minimum number of septin nucleotides or amino acids that are necessary to align the second sequence, and does not include alignment (e.g., forced alignment) with non-septin sequences, such as those fused to septin. The total number of aligned nucleotides or amino acids may correspond to the entire septin sequence or may correspond to fragments of the full-length septin sequence as defined herein.

Sequences can be aligned using the algorithm described by Altschul et al. (*Nucleic Acids Res.*, 25:3389-3402 (1997)) as incorporated into BLAST (basic local alignment search tool) programs, available at ncbi.nlm.nih.gov on the World Wide Web. BLAST searches or alignments can be performed to determine percent sequence identity between a septin nucleic acid molecule and any other sequence or portion thereof using the Altschul et al. algorithm. BLASTN is the program used to align and compare the identity between nucleic acid sequences, while BLASTP is the program used to align and compare the identity between amino acid sequences. When utilizing BLAST programs to calculate the percent identity between a septin sequence and another sequence, the default parameters of the respective programs are used.

A septin polypeptide (or fragment thereof) that can be used as described herein (e.g., to detect the presence or absence septin-specific autoantibodies and/or to treat a mammal having, or suspected of having, an autoimmune ataxia) can be from any appropriate source. In some cases, a septin polypeptide (or fragment thereof) described herein can be obtained from human, mouse, or other mammalian neuronal tissue, neuronal cell lines, or transfected cells (e.g., mammalian, *E. coli* or yeast) expressing a recombinant septin nucleic acid, or the septin polypeptide may be synthetic. In some cases, a septin polypeptide (or fragment thereof) described herein can be in a cell lysate (e.g., a whole cell lysate or a cell fraction). In some cases, a septin polypeptide (or fragment thereof) described herein can be a purified polypeptide. A "purified" polypeptide refers to a polypeptide that constitutes the major component in a mixture of components, e.g., 30% or more, 40% or more, 50% or more, 60% or more, 70% or more, 80% or more, 90% or more, 95% or more, or 99% or more by weight. Polypeptides may be purified by methods including affinity chromatography or immunosorbent affinity column. Such methods can be modified to increase the solubility of the polypeptide, and purified polypeptides can be examined for their immunogenicity using methods such as western blot or immunoprecipitation assays.

For fragments of a septin polypeptide, the fragment can be generated using any appropriate method. For example, given a septin polypeptide sequence (e.g., a septin-5 polypeptide sequence), any appropriate polypeptide fragment can be generated by, for example, proteolytic cleavage of a polypeptide or chemical synthesis.

This document also provides methods for detecting septin-specific autoantibodies (e.g., septin-5-specific autoantibodies). The presence of septin-specific autoantibodies can be used to diagnose an autoimmune ataxia associated with septin-specific autoantibodies. For example, the methods and materials described herein can be used to identify a mammal (e.g., a human) as having an autoimmune ataxia associated with septin-specific autoantibodies (e.g., having an immune system that is producing septin-specific autoantibodies) based, at least in part, on the presence of septin-specific autoantibodies in a sample obtained from the mammal. In some cases, a septin polypeptide (e.g., a septin-5 polypeptide) (or fragment thereof) described herein can be used (e.g., in various immunological techniques) to detect a septin-specific autoantibody (e.g., a septin-5-specific autoantibody). For example, a septin-5 polypeptide (or fragment thereof) described herein can be used in an immunoassay to detect septin-5-specific autoantibodies in a biological sample. In some cases, septin polypeptides (or fragment thereof) described herein can be contacted with a sample (e.g., serum) obtained from a mammal (e.g., a mammal suspected of having an autoimmune ataxia associated with septin-specific autoantibodies) under conditions where, when septin-specific autoantibodies are present, the septin polypeptides (or fragments thereof) can form a complex with the septin-specific autoantibodies (e.g., a septin/septin-specific autoantibody complex), and an immunoassay can be used to detect the complex. For example, when septin-5-specific autoantibodies are present in a sample obtained from a mammal suspected of having an autoimmune ataxia, a septin-5 polypeptide (or fragment thereof) described herein can be used to form a complex with the septin-5-specific autoantibodies (e.g., a septin-5/septin-5-specific autoantibody complex), and an immunoassay can be used to detect the complex. Examples of immunoassays that can be used to detect the presence of a septin-specific autoantibody, or a septin/septin-specific autoantibody complex include, without limitation, immunocytochemical staining techniques, immunohistochemical staining techniques, enzyme-linked immunosorbent assays (ELISA), western blot, radioimmunoassays, cell-based immunofluorescence assays, and flow cytometry.

Septin polypeptides (or fragments thereof) that can be used as described herein (e.g., to detect the presence or absence septin-specific autoantibodies and/or to treat a mammal having, or suspected of having, an autoimmune ataxia) with or without modification. In some cases, a septin polypeptide (or fragment thereof) can be modified for the detection of septin-specific autoantibodies in vitro (e.g., in an immunoassay). In some cases, a septin polypeptide (or fragment thereof) can be modified for the detection of septin-specific autoantibodies in vivo (e.g., in an in vivo imaging technique). Polypeptides (or fragment thereof) can be labeled by either covalently or non-covalently combining the polypeptide with a second substance that provides for detectable signal. A wide variety of labels and conjugation techniques can be used. Some examples of labels that can be used include radioisotopes, enzymes, substrates, cofactors, inhibitors, fluorescent agents, chemiluminescent agents, magnetic particles, and the like. In some cases, a septin polypeptide (or fragment thereof) can be conjugated to an imaging agent. Suitable imaging agents include, but are not limited to, radioisotopes, such as $^{32}P$, $^{99}Tc$, $^{111}In$ and $^{131}I$.

In some cases, anti-septin antibody (e.g., an anti-septin-5 antibody) can be used in various immunological techniques for detecting septin polypeptides (e.g., septin-5 polypeptides). In some cases, an anti-septin-5 antibody can be used (e.g., in various immunological techniques) to detect a septin-5 polypeptide. For example, an anti-septin-5 antibody can be used in an immunoassay to detect a septin-5 polypeptide. In some cases, when septin-specific autoantibodies are present in a sample, septin polypeptides can form a complex with the septin-specific autoantibodies (e.g., a septin/septin-specific autoantibody complex), and an immunoassay using an anti-septin antibody can be used to detect the complex. Examples of immunoassays that can be used to detect the presence of a septin polypeptide, or a septin/septin-specific autoantibody complex, include, without limitation, immunocytochemical staining techniques, immunohistochemical staining techniques, ELISA, western blot, radioimmunoassays, cell-based immunofluorescence assays, and flow cytometry.

Anti-septin antibodies (e.g., anti-septin-5 antibodies) can be used with or without modification for the detection of septin polypeptides (e.g., septin-5 polypeptides). Anti-septin antibodies can be labeled either directly or indirectly, and a wide variety of labels, including radioisotopes, enzymes, substrates, cofactors, inhibitors, fluorescent agents, chemiluminescent agents, and magnetic particles. In some cases, an anti-septin antibody having specific binding affinity for a septin polypeptide can be conjugated to an imaging agent. Examples of imaging agents that can be used include, without limitation, radioisotopes, such as $^{32}P$, $^{99}Tc$, $^{111}In$, and $^{131}I$.

In some cases, a mammal identified as having an autoimmune ataxia associated with septin-specific autoantibodies (e.g., having an immune system that is producing septin-specific autoantibodies) as described herein (e.g., based, at least in part, on the presence of septin-specific autoantibodies in a sample obtained from the mammal) can have the diagnosis confirmed. For example, identification of an autoimmune ataxia can be confirmed using, for example, physical examinations such as a neurological examination (e.g., for memory, concentration, vision, hearing, balance, coordination, and/or reflexes) and imaging studies such as brain imaging studies (e.g., computer tomography (CT) scanning and magnetic resonance imagining (MRI)).

This document also provides methods for treating a mammal (e.g., a human) identified as having an autoimmune ataxia (e.g., whose immune system is producing septin-specific autoantibodies such as septin-5-specific autoantibodies). In some cases, methods for treating a mammal (e.g., a human) identified as having an autoimmune ataxia associated with the presence of septin-specific autoantibodies (e.g., septin-5-specific autoantibodies) can be effective to reduce one or more symptoms of the autoimmune ataxia. Examples of symptoms of autoimmune ataxias include, without limitation, neurobehavioral phenotypes, cortical dysplasia, developmental delays, platelet dysfunction, pain, fatigue, dizziness, incoordination (e.g., resulting in falls), gait difficulties, and speech difficulties. In some cases, methods for treating a mammal (e.g., a human) identified as having an autoimmune ataxia associated with the presence of septin-specific autoantibodies (e.g., septin-5-specific autoantibodies) can be effective to remove a substantial portion of septin-specific autoantibodies present within the mammal (e.g., present within a body fluid of the mammal). As used herein, removing a "substantial portion" means removing at least 20% (e.g., at least 20%, at least 30%, at least 40%, at least 50%, at least 60%, at least 65%, at least 70%, at least 75%, at least 80%, at least 85%, at least 90%, at least 93%, at least 95%, at least 96%, at least 97%, at least 98%, at least 99%, at least 99.5%, at least 99.8%, or even 100%) of the septin-specific autoantibodies (e.g., septin-5-specific autoantibodies) that were present in the body fluid of a mammal prior to treating the mammal as described herein. The body fluid can be blood (e.g., serum or plasma) or any other body fluid, e.g., lymph or cerebrospinal fluid. In some cases, depleting septin-specific autoantibodies (e.g., septin-5-specific autoantibodies) from mammals with a autoimmune ataxia as described herein also can be effective to reduce one or more symptoms of the autoimmune ataxia.

In some cases, a mammal identified as having an autoimmune ataxia can be treated by administering to the mammal any appropriate agent or therapy used to treat an autoimmune ataxia. In some cases, an agent or therapy used to treat an autoimmune ataxia can treat one or more symptoms of an autoimmune ataxia. Examples of agents and therapies that can be used to treat ataxia include, without limitation, immunomodulatory agents such as immunosuppressants (e.g., corticosteroids, mycophenolate mofetil, azathioprine, tacrolimus, cyclophosphamide, rituximab, mTOR inhibitors, methotrexate, anti-CD19 monoclonal antibodies, and anti-Il-6 monoclonal antibodies), physical therapy, occupational therapy, and speech therapy. In some cases, septin antigen specific tolerance induction strategies or immunotherapy targeting septin-specific T cells and/or B cells can be used to treat an autoimmune ataxia associated with septin-specific autoantibodies.

In some cases, a mammal identified as having an autoimmune ataxia associated with the presence of septin-specific autoantibodies (e.g., septin-5-specific autoantibodies) can be treated using one or more septin polypeptides (e.g., one or more septin-5 polypeptides) described herein (e.g., in an apheresis method). For example, apheresis for the treatment of an autoimmune ataxia associated with septin-specific autoantibodies (e.g., septin-5-specific autoantibodies) can be used to remove septin-specific autoantibodies from a human. Methods and extracorporeal systems for apheresis (i.e., the process of withdrawing blood from a mammal, removing components from the blood, and returning the blood, or blood depleted of one or more components, to the mammal) can be used as described elsewhere (see, for example, U.S. Pat. Nos. 4,708,713; 5,258,503; 5,386,734; and 6,409,696). In some cases, an apheresis method can be used to remove septin-specific autoantibodies from a body fluid of a mammal. The method can include withdrawing a body fluid from a mammal; removing a substantial portion of septin-specific autoantibodies from the fluid; and returning the fluid to the mammal. Antibodies removed can be of any class, e.g., IgG (such as IgG1, IgG2, IgG3, IgG4), IgM, IgD, IgA, or IgE antibodies.

Removal of septin-specific autoantibodies (e.g., septin-5-specific autoantibodies) can be performed by contacting a body fluid with one or more septin polypeptides (e.g., septin-5 polypeptides) described herein. The septin polypeptide can be bound to a solid support. Such solid supports can be, without limitation, membranes, fibers, spherical beads, or granules and can be made with a water-insoluble, preferably porous, biocompatible material, e.g., organic polymers such as agarose, dextran, and polyacrylamide, or inorganic porous materials such as porous glass or porous silica gel. Such materials can be used as is or adapted (e.g., derivatized with appropriate chemical groups) for attachment of a septin polypeptide.

When the body fluid is blood, the plasma and/or white blood cells can be separated from red blood cells (e.g., erythrocytes), and the red blood cells can be returned to the mammal with or without white blood cells. In some cases, the blood cells are returned to the mammal with artificial rather than their original blood plasma. The "replacement fluid" (e.g., physiological saline) can be administered to the mammal after removal of the fluid. In some cases, the septin-specific autoantibodies (e.g., septin-5-specific autoantibodies) can be selectively removed from the blood plasma in the course of apheresis, and the blood cells can be mixed with the septin-specific autoantibody-depleted plasma and then re-infused as a mixture into the mammal.

The system can be a continuous one in which, for example, blood is pumped out of a blood vessel (e.g., an artery or a vein) passed over a solid support derivatized with septin polypeptides (e.g., septin-5 polypeptides) described herein and pumped directly back into a blood vessel of the mammal. As in non-continuous systems, blood cells can be separated from plasma prior to passing of the plasma over the solid support.

In cases where septin polypeptides (e.g., septin-5 polypeptides) described herein are used in an apheresis method to treat a mammal (e.g., a human) having an autoimmune ataxia, the methods also can include administering to the mammal any appropriate agent or therapy used to treat an autoimmune ataxia described herein. In cases where a mammal having an autoimmune ataxia is treated with one or more septin polypeptides described herein and is treated with agents or therapies used to treat an autoimmune ataxia described herein, the agents or therapies used to treat an autoimmune ataxia can be administered at the same time or independently. For example, one or more septin polypeptides described herein and one or more agents or therapies used to treat an autoimmune ataxia can be formulated together to form a single composition. In some cases, one or more septin polypeptides described herein can be administered first, and the one or more agents or therapies used to treat an autoimmune ataxia administered second, or vice versa.

This document also provides articles of manufacture (e.g., kits) containing one or more septin polypeptides described herein (e.g., one or more septin-5 polypeptides described herein). Septin polypeptides (e.g., septin-5 polypeptides) described herein that are included in an article of manufacture as described herein can be provided within a cell, in a solution in which they are soluble, or in a lyophilized form. The kit may further include a second substance that, for example, provides for detection of a septin polypeptide/anti-septin autoantibody complex. Such substances can be an anti-septin antibody (e.g., an anti-septic-5 antibody), an anti-IgG antibody (e.g., an anti-human IgG antibody), or combinations thereof. Such substances can include a covalently linked detectable label (e.g., a fluorescent label). In addition, a kit can include directions for using the septin polypeptides and/or directions for practicing a method described herein (i.e., detecting septin-specific autoantibodies in a biological sample). For example, a kit can include directions for using the septin-5 polypeptides and/or directions for practicing a method described herein (e.g., detecting septin-5-specific autoantibodies in a biological sample).

The invention will be further described in the following examples, which do not limit the scope of the invention described in the claims.

EXAMPLES

Example 1

Autoimmune Septin-5 Cerebellar Ataxia

Patients and Methods
Study Population 367 archived specimens (serum, 334; CSF, 33) from patients for whom tissue-based immunofluorescence assay (IFA) screening had demonstrated a pattern of diffuse neural synaptic (neuropil) antibody staining resembling, but not meeting criteria for, amphiphysin-IgG (as described in, for example, Honorat et al., 2017 *Neurol Neuroimmunol Neuroinflamm* 4:e385). Archived specimens with that designation were retested by IFA and classified according to their staining patterns. Clinical information was obtained by medical record review.

Antigen Preparation

Cytosolic and membrane preparations were used. For the cytosolic antigen preparation, adult mouse cerebellum and cerebrum were homogenized with buffer, 2 ml/g (10 mM Hepes, 1 mM $MgCl_2$, 1 mM ethylenediaminetetraacetic acid, and complete protease inhibitor cocktail [Roche, Indianapolis, USA]). Homogenate was clarified by centrifugation (50000×g, 15 minutes) and supernatant was stored at −80° C. For the membrane preparation, pellet from the cytosolic preparation was resuspended in NP-40 buffer (1% NP-40, 0.1% SDS, 0.15 M NaCl, 0.01 M $NaPO_4$ pH 7.2, 2 mM EDTA, and complete protease inhibitor cocktail [Roche, Indianapolis, USA]) for 2 hours then centrifuged at 100000×g for 45 minutes. Supernatant was stored at −80° C.

Western Blotting, Immunoprecipitation, & Mass Spectrometry

For western blot, mouse cytosolic or membrane cerebellar extract was separated on 4-15% or 10% polyacrylamide gels, and the membrane was probed with sera from healthy subjects and patients (1:200 dilution), and commercial septin-5-specific IgG (1:5000). Recombinant full length septin- 4, septin-5 and septin-7 proteins were used for western blot (Abcam, San Francisco, Calif., USA).

For immunoprecipitation, serum of 2 patients (patients 2 and 6) was pooled then IgG was purified using protein G sepharose. The IgG were eluted from the protein G complex by acetic acid and dialyzed using a 10000 MCWO membrane (Thermo Scientific, Rockford, Ill., USA) in PBS then HEPES buffer. The collected IgG was bound to Affi-Gel (9:1.5 ratio) rotating at 4° C. for 4 hours (Bio-Rad, Hercules, Calif., USA). The complex was washed in various buffers (NP-406 Murea, then again in NP-40) and exposed to cerebellar membrane protein extract (overnight, 4° C.). After washing, the antigen was eluted with 6 M urea buffer (6 M urea, 2% Chaps). The eluted sample was electrophoresed using a 10% polyacrylamide gel, and proteins were located by silver staining and by western blot. The immunoreactive bands were excised from the stained gel and analyzed by high pressure liquid chromatography electrospray tandem mass spectrometry.

Plasmid Constructs

Human full-length SEPT5 cDNAs were cloned into pcDNA3.1+/C-(K)DYK+N-eGFP (green fluorescent protein) vectors (GenScript, Piscataway, N.J., USA). All of the plasmid constructs were verified by Sanger DNA sequencing.

Cell Based Immunofluorescence Assay (CBA)

HEK293 cells stably transfected with GFP-tagged Sept5 cDNA (isoform 1) were generated and used for CBA. Cells were plated in 8-well poly-D-lysine-coated chamber slides (Corning, Corning, N.Y.), fixed in 4% paraformaldehyde and permeabilized with Triton-X-100. Patient or control serum (1:200 dilution), CSF (1:10) or commercial septin-5-IgG (1:500) were added to the cells for 45 to 60 minutes at room temperature. Secondary antibody (TRITC-conjugated goat antihuman, anti-rabbit or anti-mouse IgG, 1:400) was applied for 30 minutes.

Protein Microarray

This experiment was conducted by ThermoFischer Scientific utilizing the Human ProtoArray v5.0; Invitrogen. Nine thousand purified human proteins were printed in nitrocellulose-coated microarray slides. The slides were blocked in blocking buffer (50 mM HEPES, 200 mM NaCl, 0.01% Triton X-100, 25% glycerol, 20 mM reduced glutathione, 1.0 mM DTT, 1× synthetic block) at 4° C. for 1 hour. The slides were rinsed in PBST buffer then probed with serum from patients or controls (1:500) for 90 minutes at 4° C. with gentle agitation. The slides were washed 5 times and incubated (90 minutes, 4° C.) with an Alexa Fluor 647-conjugated goat anti-human IgG antibody (1 μg/ml). The slides were washed and dried by spinning. The microarray slides were then scanned using a GenePix 4000B fluorescent microarray scanner.

Results

Characterization of the Antigen

Immunohistochemical Distribution of the Neural Antigen.

Indirect IFA of patients' serums and CSF using cryosections of murine brain tissue demonstrated a novel identical staining pattern in 6 patients (FIG. 1A-1F). Specimens strongly stained synaptic regions (neuropil) of mouse cerebrum and cerebellum. The molecular layer of the cerebellum and the thalamus demonstrated stronger immunoreactivity than midbrain, hippocampus, cortex and basal ganglia. The myenteric plexus of the gastric mucosa and the renal glomeruli were also reactive in all cases. The staining pattern superficially resembled that produced by gamma amino butyric acid $(GABA)_B$ receptor antibody; all were negative by cell-based assay (CBA) for that antibody.

Identification and Confirmation of Septin-5 as Antigen

Figure 1A:
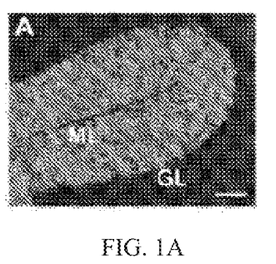
FIG. 1A shows immunofluorescence patterns of patient IgG binding to mouse tissues, where patient serum produces synaptic staining patterns of cerebellar molecular layer (ML) and granular layer (GL).
Figure 1B:
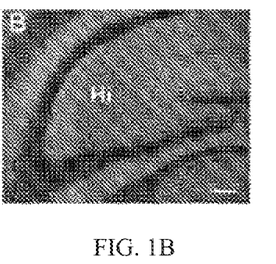
FIG. 1B shows immunofluorescence patterns of patient IgG binding to mouse tissues, where patient serum produces synaptic staining patterns of hippocampus (Hi).
Figure 1C:
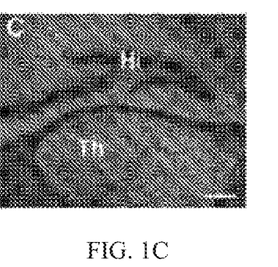
FIG. 1C shows immunofluorescence patterns of patient IgG binding to mouse tissues, where patient serum produces synaptic staining patterns of hippocampus (Hi) and thalamus (Th).
Figure 1D:
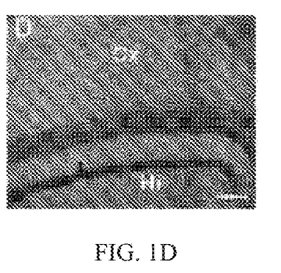
FIG. 1D shows immunofluorescence patterns of patient IgG binding to mouse tissues, where patient serum produces synaptic staining patterns of hippocampus (Hi) and cerebral cortex (Cx).
Figure 1E:
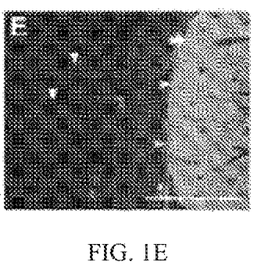
FIG. 1E shows immunofluorescence patterns of patient IgG binding to mouse tissues, where patient serum produces synaptic staining patterns of enteric ganglia (arrow) and nerves (arrow heads).
Figure 1F:
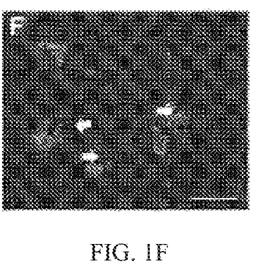
FIG. 1F shows immunofluorescence patterns of patient IgG binding to mouse tissues, where patient serum produces synaptic staining patterns of renal glomeruli (arrows).
Figure 1G:
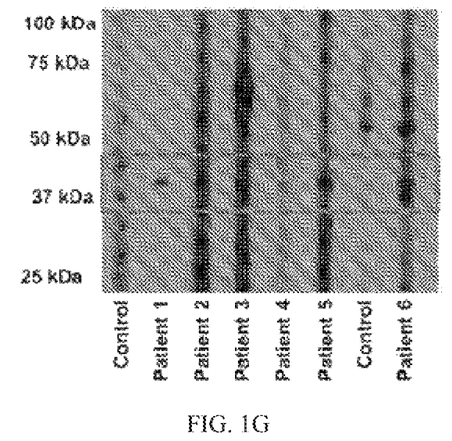
FIG. 1G shows mouse cerebrum proteins, reduced, denatured and separated electrophoretically produced a ~45 KDa band when probed with patients IgGs (patient 1-6) but not healthy control subject IgGs.
Figure 1H:
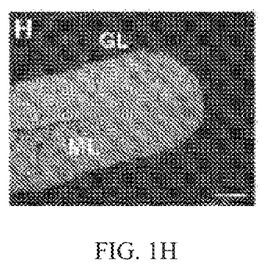
FIG. 1H shows application of IgG eluted from a nitrocellulose strip containing the ~45 KDa band to mouse tissue reproduced the patient IgG staining pattern. Scale bar=5 mm.
Figure 1I:
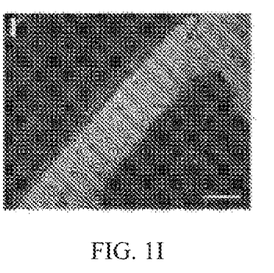
FIG. 1I shows application of IgG eluted from a nitrocellulose strip containing the ~45 KDa band to mouse tissue reproduced the patient IgG staining pattern. Scale bar=5 mm.

Immunoblotting of mouse brain lysates with serums revealed a common immunoreactive band with approximate molecular weight of 45 kDa among patients only (FIG. 1G). A patient serum and purified IgG eluted from that patient's 45 kDa demonstrated the same pattern of IgG staining by IFA (FIGS. 1H and 1I). To identify the target antigen, immunoprecipitation of mouse cerebellar extract was performed using IgGs from patients 2 and 6. Analysis by in-gel digestion and mass spectrometry of proteins captured by IgGs from those 2 patients, immobilized by Affi-Gel, assigned the greater number of polypeptides to septin-5 (43 kDa).

Figure 2A:
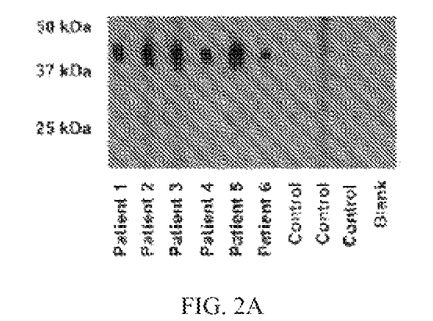
FIG. 2A shows confirmation of septin-5 as a target antigen of autoimmune ataxia. A western blot shows IgG in all 6 patients' serums binding to septin-5 recombinant protein (lanes 1-6); IgG in healthy controls' serums are non-reactive (lanes 7-9).
Figure 2B:
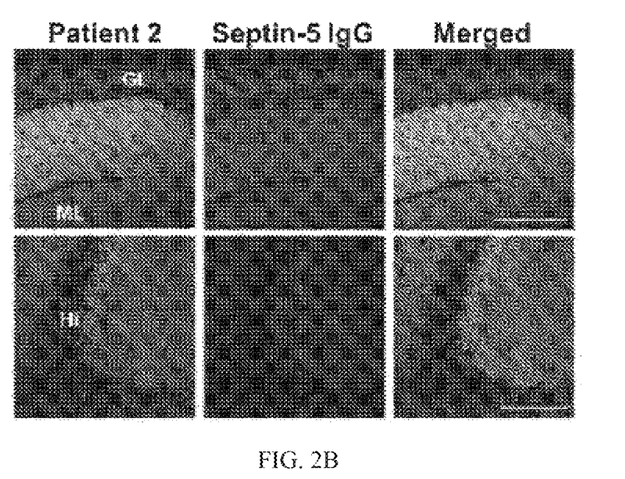
FIG. 2B shows confocal microscopy where patient IgG co-localizes with septin-5 immunoreactivity in mouse cerebellum (top row) and hippocampus (bottom row). Left column; patient-IgG; middle column, commercial septin-5 IgG; right column, merged images.
Figure 2C:
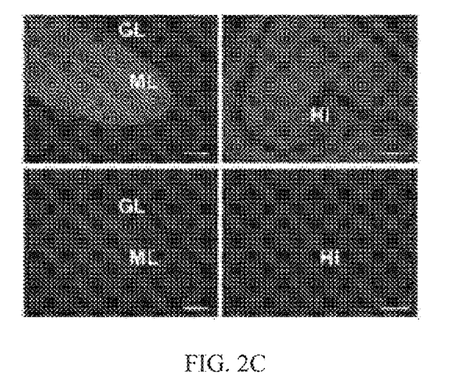
FIG. 2C shows immune absorption of patient IgG by septin-5 recombinant protein: cerebellum, left column; hippocampus, right column.

In order to confirm septin-5 as the antigen of interest, firstly, a recombinant form of septin-5 protein was used for western blot analysis and probed with serum. Serums from patients 1 to 6, but not control serums, demonstrated strong immunoreactivity with septin-5 (FIG. 2A). Secondly, IFA demonstrated co-localization between commercial septin-5 IgG and patient-IgG on mouse brain tissue (FIG. 2B). Thirdly, mouse brain immunoreactivity of patients' IgG was abrogated by the absorption of a patient's serum with septin-5 recombinant protein (FIG. 2C). Fourthly, patients' serums and CSF were tested by indirect IFA on septin-5-transfected HER 293 cells (CBA, FIGS. 3A-I). Serums and CSF of all 6 patients were reactive with septin-5 (isoform 1 only), and all controls were negative. Finally, the screening protein microarray was used in a blinded fashion to analyze the antibody profiles in serums available from 5 of the 6 patients (patients 1-5) and 5 controls (healthy and known to be neural antibody negative in our laboratory). Candidate autoantigens are shown in Table 1.

TABLE 1

Candidate autoantigens with elevated signal in the Group 1 (Disease) samples relative to the Group 2 (Normal) samples.

| | Count | | | | Relative fluorescence units | | | Mean Ratio | |
| --- | --- | --- | --- | --- | --- | --- | --- | --- | --- |
| | Disease | Normal | | | | | | | |
| Database ID | Group, N | Group, N | P-Value | Cutoff | Negative Signal | Disease Group | Normal Group | (Disease/Normal) | Protein name (Gene ID) |
| NM_002688.2 | 5 | 0 | 0.004 | 3031 | 104 | 47020 | 2086 | 22.5 | Septin 5 (SEPT5) |
| NM_004574.2 | 4 | 0 | 0.024 | 946 | 48 | 11296 | 523 | 21.6 | Septin 4 (SEPT4), transcript variant 1 |
| BC029220.1 | 4 | 0 | 0.024 | 4400 | 125 | 21173 | 2237 | 9.5 | Transcription factor SOX-5 |
| NM_198266.1 | 5 | 1 | 0.024 | 2343 | 239 | 19490 | 2182 | 8.9 | Inhibitor of growth family, member 3 (ING3), transcript variant 2 |

TABLE 1-continued

Candidate autoantigens with elevated signal in the Group 1 (Disease) samples relative to the Group 2 (Normal) samples.

| Database ID | Count Disease Group, N | Count Normal Group, N | P-Value | Cutoff | Relative fluorescence units Negative Signal | Relative fluorescence units Disease Group | Relative fluorescence units Normal Group | Mean Ratio (Disease/Normal) | Protein name (Gene ID) |
|---|---|---|---|---|---|---|---|---|---|
| BC015752.1 | 4 | 0 | 0.024 | 1500 | 42 | 7306 | 843 | 8.7 | Interferon regulatory factor 4 (IRF4) |
| NM_001005339.1 | 5 | 1 | 0.024 | 2557 | 487 | 19932 | 2455 | 8.1 | Regultor of G-protein signaling 10 (RGS10), transcript variant 1 |
| NM_024946.1 | 5 | 0 | 0.004 | 4179 | 113 | 22185 | 2916 | 7.6 | NEFA-interacting nuclear protein NIP30 (NIP30) |
| NM_014110.3 | 4 | 0 | 0.024 | 5988 | 539 | 32701 | 4332 | 7.5 | Protein phosphatase 1, regulatory (inhibitor) subunit 8 (PPP1R8), transcript variant 1 |
| BC040946.1 | 4 | 0 | 0.024 | 4224 | 211 | 19544 | 2697 | 7.2 | CWC15 homolog (S. cerevisiae) (HSPC148) |
| NM_001007246.1 | 4 | 0 | 0.024 | 2819 | 72 | 8765 | 1391 | 6.3 | Bromodomain and WD repeat domain containing 1 (BRWD1), transcript variant 3 |
| BC047064.1 | 4 | 0 | 0.024 | 1904 | 732 | 9199 | 1463 | 6.3 | SRY (sex determining region Y)-box 6, mRNA (cDNA clone MGC: 48285 IMAGE: 5269193), complete cds |
| NM_207350.1 | 4 | 0 | 0.024 | 2112 | 47 | 7167 | 1196 | 6.0 | Similar to FRG1 protein (FSHD region gene 1 protein) (MGC72104) |
| NM_001788.3 | 4 | 0 | 0.024 | 979 | 57 | 2815 | 476 | 5.9 | Septin 7 (SEPT7), transcript variant 1 |
| NM_130777.1 | 4 | 0 | 0.024 | 3065 | 74 | 8141 | 1409 | 5.8 | X antigen family, member 2 (XAGE2) |
| BC005004.1 | 4 | 0 | 0.024 | 3018 | 532 | 9406 | 1685 | 5.6 | family with sequence similarity 64, member A (FAM64A) |
| BC015803.1 | 4 | 0 | 0.024 | 3241 | 211 | 10759 | 2138 | 5.0 | interferon regulatory factor 2 (IRF2) |
| NM_138640.1 | 4 | 0 | 0.024 | 2589 | 75 | 8869 | 1768 | 5.0 | golgi associated, gamma adaptin ear containing, ARF binding protein 2 (GGA2), transcript variant 2 |
| NM_153498.1 | 4 | 0 | 0.024 | 2105 | 66 | 4822 | 1064 | 4.5 | calcium/calmodulin-dependent protein kinase ID (CAMK1D), transcript variant 2 |
| NM_014891.1 | 4 | 0 | 0.024 | 7880 | 3421 | 21504 | 4850 | 4.4 | PDGFA associated protein 1 (PDAP1) |
| NM_002904.4 | 4 | 0 | 0.024 | 6903 | 5463 | 15464 | 3957 | 3.9 | RD RNA binding protein 1 (RDBP) |
| BC051687.1 | 4 | 0 | 0.024 | 3119 | 63 | 6520 | 1704 | 3.8 | Kruppel-like factor 3 (basic) (KLF3) |
| BC066938.1 | 5 | 1 | 0.024 | 2268 | 323 | 9704 | 2580 | 3.8 | DEAD (Asp-Glu-Ala-Asp) box polypeptide 43 (DDX43) |
| BC051733.1 | 4 | 0 | 0.024 | 3099 | 112 | 5755 | 1581 | 3.6 | Leucine zipper protein 1, mRNA (cDNA clone MGC: 51018 IMAGE: 4838475), complete cds |
| NM_005720.1 | 4 | 0 | 0.024 | 1293 | 54 | 2854 | 810 | 3.5 | actin related protein 2/3 complex, submit 1B, 41 kDa (ARPC1B) |
| BC050616.1 | 4 | 0 | 0.024 | 1316 | 337 | 2368 | 762 | 3.1 | tumor suppressing subtransferable candidate 4 (TSSC4) |
| BC008288.1 | 5 | 1 | 0.024 | 953 | 50 | 2758 | 902 | 3.1 | UBX domain containing 1 (UBXD1) |
| BC014924.1 | 4 | 0 | 0.024 | 6634 | 783 | 10051 | 3940 | 2.6 | kinesin family member 2C (KIF2C) |
| BC013009.1 | 4 | 0 | 0.024 | 1789 | 50 | 3080 | 1304 | 2.4 | zinc finger, MYM-type 3 (ZMYM3) |
| NM_001156.2 | 4 | 0 | 0.024 | 1473 | 35 | 2508 | 1129 | 2.2 | annexin A7 (ANXA7), transcript variant 1 |
| NM_002596.2 | 4 | 0 | 0.024 | 1862 | 391 | 2329 | 1137 | 2.0 | PCTAIRE protein kinase 3 (PCTK3), transcript variant 3, mRNA |
| NM_178425.1 | 4 | 0 | 0.024 | 1576 | 92 | 2022 | 1005 | 2.0 | histone deacetylase 9 (HDAC9), transcript variant 5 |

Septin-5 was identified as the top candidate autoantigen among all patient serums, and was not a candidate antigen in any of the controls. In each patient serum, septin-5 had the highest fold change in signal intensity relative to the controls and the lowest p-value. Because septin-4 and septin-7 were also identified as possible lower probability candidates, western blots utilizing recombinant forms of those proteins were undertaken using all 6 patient serums. Patient 3 alone had septin-4-IgG detected.

Clinical Features

Four of the 6 patients were female. The median age of symptom onset was 59 years (range, 47-62). The median septin 5-IgG antibody value in serum for the 6 patients was 1:15360 (range, 1:7680-1:15,360; normal value≤120).

Clinical information was available for 4 patients (2 men, 2 women; Table 2), median follow-up duration was 35 months (range, 1-77).

TABLE 2

Clinical, testing, treatment and outcome data for 4 patients with autoimmune septin-5 cerebellar ataxia.

| Patient No./Sex/Age/Race | Clinical summary | Cancer | Septin-5 Ig-G+ | Coexisting antibodies (nmol/L) | Coexisting autoimmune disease | Inflammatory CSF finding | MRI brain |
|---|---|---|---|---|---|---|---|
| 2/F/60/C | Subacute onset vertigo, intractable nausea and vomitting. initially diagnosed as labarynthitis followed by gait ataxia | No | Serum & CSF | None | No | NA | Normal |
| 3/M/62/NA | Rapidly progressive eye movement disorder. truncal/limb myoclonus, followed by encephialopathy | NA | Serum & CSF | GAD65 0.17 Septin-4 | NA | NA | NA |
| 4/F/59/AA | Rapidly progressive spinocerebellar syndrome with tremor | No (investigations including age-related cancer screening & PET scan) | Serum & CSF | CCN 0.06 | No | NA | NA |
| 5/M/47/C | Headache followed by subacute cerebellar ataxia, & prominent oscillopsia | No (investigations including age-related cancer screening, & CT body, & ultrasound of testes) | Serum (CSF NA) | CCN 0.14. GAD65 28.1 | No | Protein 70 mg/dL; elevated IgG synthesis rate | Cerebellar vermis atrophy |

| Patient No./Sex/Age/Race | Immunotherapy (Improved?) | Neurologic nadir | Neurologic zenith | mRS at last F/U | Disease-duration (symptoms onset to last follow up/death, months) |
|---|---|---|---|---|---|
| 2/F/60/C | None, resolved spontaneously | Use of walker | Ambulated independently | 0 | 77 |
| 3/M/62/NA | NA | NA | NA | NA | 1 |
| 4/F/59/AA | Oral steroids. PLEX (initially) | Bedbound | Death | 6 | 6 |
| 5/M/47/C | IVMP followed by IVIg maintenance (Yes) | Use of cane | Ambulated independently, with residual ataxic signs | 1 | 54 |

AA = African-American; C = Caucasian; CCN = N-type calcium channel antibody; CT = computerized tomography; F = female; F/U = follow-up; GAD65 = glutamic acid decarboxylase, 65 kDa isoform; IVMP = intravenous methylprednisolone; IVIg = intravenous immune globulin; M = male; mRS = modified Rankin score; NA = not available; NO. = number; PET = positron emission tomography; PLEX = plasma exchange.

Figure 2D:
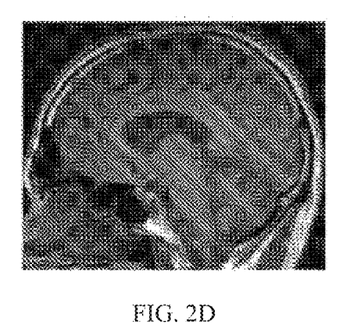
FIG. 2D shows T1 sagittal MRI of head from Patient 3 demonstrating cerebellar atrophy. GL=granular layer; ML=molecular layer. Hi=hippocampus. Scale bar=5 mm.
Figure 3A:
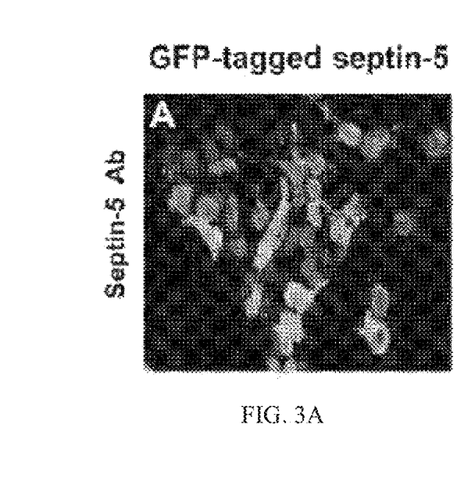
FIG. 3A shows IgG binding to HEK293 cells transfected with expression plasmids encoding green fluorescent protein-tagged human Septin-5 isoform 1. Commercial septin-5 antibody stains septin 5-(isoform 1)-transfected GFP-tagged HEK 293 cells.
Figure 3B:
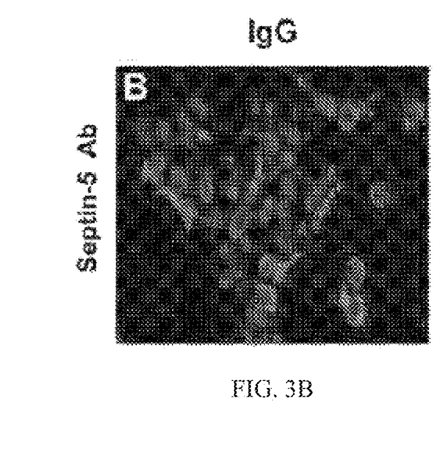
FIG. 3B shows IgG binding to HEK293 cells transfected with expression plasmids encoding green fluorescent protein-tagged human Septin-5 isoform 1. Commercial septin-5 antibody stains septin 5-(isoform 1)-transfected GFP-tagged HEK 293 cells.
Figure 3C:
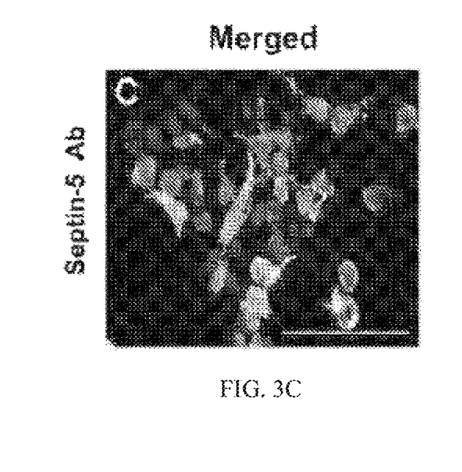
FIG. 3C shows IgG binding to HEK293 cells transfected with expression plasmids encoding green fluorescent protein-tagged human Septin-5 isoform 1. Commercial septin-5 antibody stains septin 5-(isoform 1)-transfected GFP-tagged HEK 293 cells. Scale bar=5 mm.
Figure 3D:
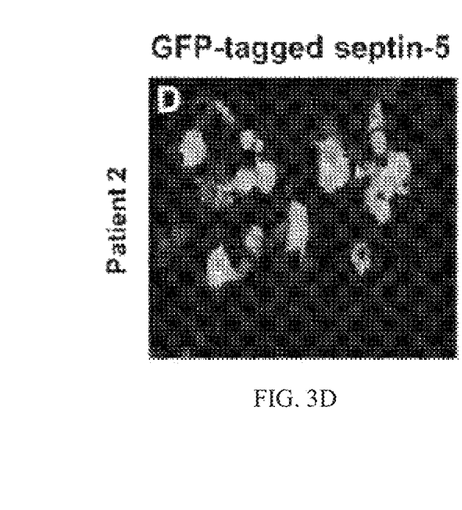
FIG. 3D shows IgG binding to HEK293 cells transfected with expression plasmids encoding green fluorescent protein-tagged human Septin-5 isoform 1. Patient serum stains septin 5-(isoform 1)-transfected GFP-tagged HEK 293 cells.
Figure 3E:
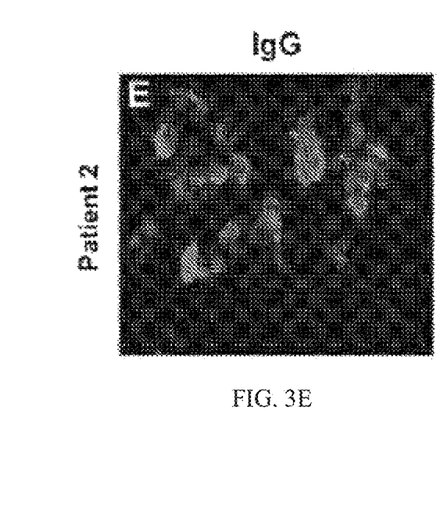
FIG. 3E shows IgG binding to HEK293 cells transfected with expression plasmids encoding green fluorescent protein-tagged human Septin-5 isoform 1. Patient serum stains septin 5-(isoform 1)-transfected GFP-tagged HEK 293 cells.
Figure 3F:
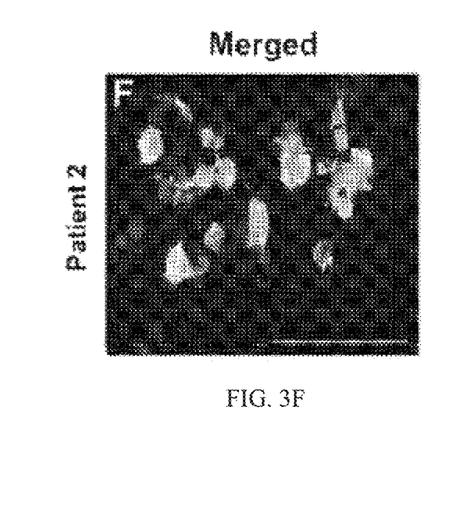
FIG. 3F shows IgG binding to HEK293 cells transfected with expression plasmids encoding green fluorescent protein-tagged human Septin-5 isoform 1. Patient serum stains septin 5-(isoform 1)-transfected GFP-tagged HEK 293 cells. Scale bar=5 mm.
Figure 3G:
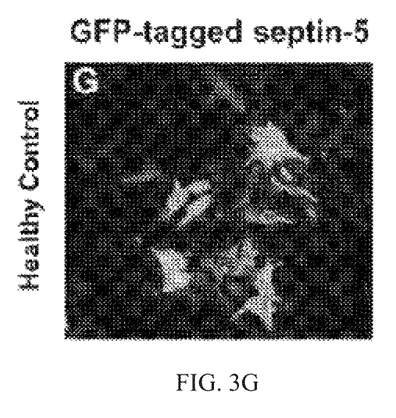
FIG. 3G shows IgG binding to HEK293 cells transfected with expression plasmids encoding green fluorescent protein-tagged human Septin-5 isoform 1. Healthy control serum does not stain septin 5-(isoform 1)-transfected GFP-tagged HEK 293 cells.
Figure 3H:
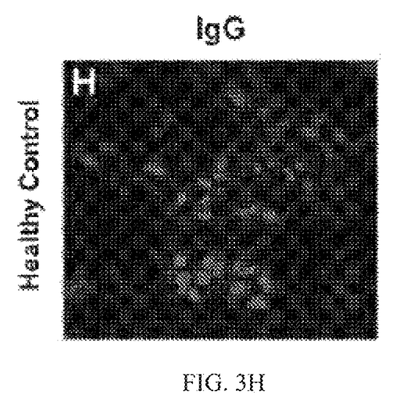
FIG. 3H shows IgG binding to HEK293 cells transfected with expression plasmids encoding green fluorescent protein-tagged human Septin-5 isoform 1. Healthy control serum does not stain septin 5-(isoform 1)-transfected GFP-tagged HEK 293 cells.
Figure 3I:
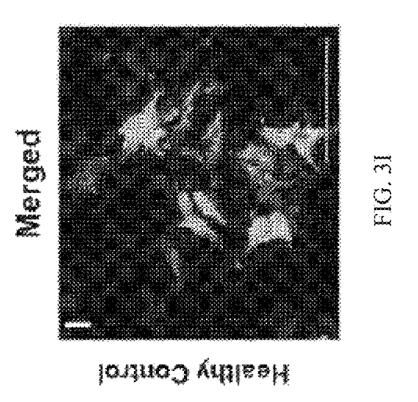
FIG. 3I shows IgG binding to HEK293 cells transfected with expression plasmids encoding green fluorescent protein-tagged human Septin-5 isoform 1. Healthy control serum does not stain septin 5-(isoform 1)-transfected GFP-tagged HEK 293 cells. Scale bar=5 mm.

All 4 patients had a cerebellar syndrome of subacute onset and rapid progression. One patient had severe vertigo, nausea and vomiting at onset, before developing a rapidly progressive cerebellar ataxia. Two other patients had prominent oscillopsia at onset. Two patients had accompanying tremulousness. One patient became encephalopathic and obtunded later in the clinical course. The one patient with routine CSF parameters available had an elevated IgG synthesis rate. Head MM (available in 2) demonstrated cerebellar atrophy in 1 (FIG. 2D) and was unremarkable in 1. None had cancer identified. One patient spontaneously recovered. Immunotherapies employed in 2 other patients with treatment and outcome data available included corticosteroids (2), plasma exchange (1), and intravenous immune globulin (1). Improvements were robust and sustained in 1 patient and transient in one (the patient died 6 months later).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method, comprising:
   (a) contacting a biological sample from a patient having immunotherapy-responsive autoimmune cerebellar ataxia, said patient having septin-5-specific autoantibodies, with a septin-5 polypeptide to form a septin-5/septin-5-specific autoantibody complex; and
   (b) detecting the presence or absence of said complex.

2. The method of claim 1, wherein said method comprises performing a western blot to detect said complex.

3. The method of claim 1, wherein said biological sample is selected from the group consisting of whole blood, serum, plasma, and cerebrospinal fluid.

* * * * *

SEQUENCE LISTING

<160> NUMBER OF SEQ ID NOS: 2

<210> SEQ ID NO 1
<211> LENGTH: 369
<212> TYPE: PRT

<213> ORGANISM: Homo sapiens

<400> SEQUENCE: 1

```
Met Ser Thr Gly Leu Arg Tyr Lys Ser Lys Leu Ala Thr Pro Glu Asp
1               5                   10                  15
Lys Gln Asp Ile Asp Lys Gln Tyr Val Gly Phe Ala Thr Leu Pro Asn
            20                  25                  30
Gln Val His Arg Lys Ser Val Lys Gly Phe Asp Phe Thr Leu Met
        35                  40                  45
Val Ala Gly Glu Ser Gly Leu Gly Lys Ser Thr Leu Val His Ser Leu
    50                  55                  60
Phe Leu Thr Asp Leu Tyr Lys Asp Arg Lys Leu Leu Ser Ala Glu Glu
65                  70                  75                  80
Arg Ile Ser Gln Thr Val Glu Ile Leu Lys His Thr Val Asp Ile Glu
                85                  90                  95
Glu Lys Gly Val Lys Leu Lys Leu Thr Ile Val Asp Thr Pro Gly Phe
            100                 105                 110
Gly Asp Ala Val Asn Asn Thr Glu Cys Trp Lys Pro Ile Thr Asp Tyr
        115                 120                 125
Val Asp Gln Gln Phe Glu Gln Tyr Phe Arg Asp Glu Ser Gly Leu Asn
    130                 135                 140
Arg Lys Asn Ile Gln Asp Asn Arg Val His Cys Cys Leu Tyr Phe Ile
145                 150                 155                 160
Ser Pro Phe Gly His Gly Leu Arg Pro Val Asp Val Gly Phe Met Lys
                165                 170                 175
Ala Leu His Glu Lys Val Asn Ile Val Pro Leu Ile Ala Lys Ala Asp
            180                 185                 190
Cys Leu Val Pro Ser Glu Ile Arg Lys Leu Lys Glu Arg Ile Arg Glu
        195                 200                 205
Glu Ile Asp Lys Phe Gly Ile His Val Tyr Gln Phe Pro Glu Cys Asp
    210                 215                 220
Ser Asp Glu Asp Glu Asp Phe Lys Gln Gln Asp Arg Glu Leu Lys Glu
225                 230                 235                 240
Ser Ala Pro Phe Ala Val Ile Gly Ser Asn Thr Val Val Glu Ala Lys
                245                 250                 255
Gly Gln Arg Val Arg Gly Arg Leu Tyr Pro Trp Gly Ile Val Glu Val
            260                 265                 270
Glu Asn Gln Ala His Cys Asp Phe Val Lys Leu Arg Asn Met Leu Ile
        275                 280                 285
Arg Thr His Met His Asp Leu Lys Asp Val Thr Cys Asp Val His Tyr
    290                 295                 300
Glu Asn Tyr Arg Ala His Cys Ile Gln Gln Met Thr Ser Lys Leu Thr
305                 310                 315                 320
Gln Asp Ser Arg Met Glu Ser Pro Ile Pro Ile Leu Pro Leu Pro Thr
                325                 330                 335
Pro Asp Ala Glu Thr Glu Lys Leu Ile Arg Met Lys Asp Glu Glu Leu
            340                 345                 350
Arg Arg Met Gln Glu Met Leu Gln Arg Met Lys Gln Gln Met Gln Asp
        355                 360                 365
Gln
```

<210> SEQ ID NO 2
<211> LENGTH: 478
<212> TYPE: PRT

<213> ORGANISM: Homo sapiens

<400> SEQUENCE: 2

Met Asp Arg Ser Leu Gly Trp Gln Gly Asn Ser Val Pro Glu Asp Arg
1               5                   10                  15

Thr Glu Ala Gly Ile Lys Arg Phe Leu Glu Asp Thr Thr Asp Asp Gly
            20                  25                  30

Glu Leu Ser Lys Phe Val Lys Asp Phe Ser Gly Asn Ala Ser Cys His
        35                  40                  45

Pro Pro Glu Ala Lys Thr Trp Ala Ser Arg Pro Gln Val Pro Glu Pro
    50                  55                  60

Arg Pro Gln Ala Pro Asp Leu Tyr Asp Asp Leu Glu Phe Arg Pro
65                  70                  75                  80

Pro Ser Arg Pro Gln Ser Ser Asp Asn Gln Gln Tyr Phe Cys Ala Pro
                85                  90                  95

Ala Pro Leu Ser Pro Ser Ala Arg Pro Arg Ser Pro Trp Gly Lys Leu
            100                 105                 110

Asp Pro Tyr Asp Ser Ser Glu Asp Asp Lys Glu Tyr Val Gly Phe Ala
        115                 120                 125

Thr Leu Pro Asn Gln Val His Arg Lys Ser Val Lys Lys Gly Phe Asp
    130                 135                 140

Phe Thr Leu Met Val Ala Gly Glu Ser Gly Leu Gly Lys Ser Thr Leu
145                 150                 155                 160

Val Asn Ser Leu Phe Leu Thr Asp Leu Tyr Arg Asp Arg Lys Leu Leu
                165                 170                 175

Gly Ala Glu Glu Arg Ile Met Gln Thr Val Glu Ile Thr Lys His Ala
            180                 185                 190

Val Asp Ile Glu Glu Lys Gly Val Arg Leu Arg Leu Thr Ile Val Asp
        195                 200                 205

Thr Pro Gly Phe Gly Asp Ala Val Asn Asn Thr Glu Cys Trp Lys Pro
    210                 215                 220

Val Ala Glu Tyr Ile Asp Gln Gln Phe Glu Gln Tyr Phe Arg Asp Glu
225                 230                 235                 240

Ser Gly Leu Asn Arg Lys Asn Ile Gln Asp Asn Arg Val His Cys Cys
                245                 250                 255

Leu Tyr Phe Ile Ser Pro Phe Gly His Gly Leu Arg Pro Leu Asp Val
            260                 265                 270

Glu Phe Met Lys Ala Leu His Gln Arg Val Asn Ile Val Pro Ile Leu
        275                 280                 285

Ala Lys Ala Asp Thr Leu Thr Pro Pro Glu Val His Lys Lys Arg
    290                 295                 300

Lys Ile Arg Glu Glu Ile Glu His Phe Gly Ile Lys Ile Tyr Gln Phe
305                 310                 315                 320

Pro Asp Cys Asp Ser Asp Glu Asp Glu Asp Phe Lys Leu Gln Asp Gln
                325                 330                 335

Ala Leu Lys Glu Ser Ile Pro Phe Ala Val Ile Gly Ser Asn Thr Val
            340                 345                 350

Val Glu Ala Arg Gly Arg Arg Val Arg Gly Arg Leu Tyr Pro Trp Gly
        355                 360                 365

Ile Val Glu Val Glu Asn Pro Gly His Cys Asp Phe Val Lys Leu Arg
    370                 375                 380

Thr Met Leu Val Arg Thr His Met Gln Asp Leu Lys Asp Val Thr Arg
385                 390                 395                 400

-continued

```
Glu Thr His Tyr Glu Asn Tyr Arg Ala Gln Cys Ile Gln Ser Met Thr
            405                 410                 415

Arg Leu Val Val Lys Glu Arg Asn Arg Asn Lys Leu Thr Arg Glu Ser
            420                 425                 430

Gly Thr Asp Phe Pro Ile Pro Ala Val Pro Pro Gly Thr Asp Pro Glu
            435                 440                 445

Thr Glu Lys Leu Ile Arg Glu Lys Asp Glu Glu Leu Arg Arg Met Gln
    450                 455                 460

Glu Met Leu His Lys Ile Gln Lys Gln Met Lys Glu Asn Tyr
465                 470                 475
```